United States Patent
Shiau

(10) Patent No.: US 11,712,518 B2
(45) Date of Patent: Aug. 1, 2023

(54) INFUSION SET WITH CAPABILITY OF CONTROLLING QUANTITY OF AN INJECTION INFUSED TO A LIMB AND SYSTEM FOR DETECTING AND CONTROLLING DRIP RATE OF AN INFUSION DEVICE

(71) Applicant: POLARAY TECHNOLOGY CORP., New Taipei (TW)

(72) Inventor: Vincent Shiau, Taipei (TW)

(73) Assignee: POLARAY TECHNOLOGY CORP., New Taipei (TW)

( * ) Notice: Subject to any disclaimer, the term of this patent is extended or adjusted under 35 U.S.C. 154(b) by 286 days.

(21) Appl. No.: 17/145,386

(22) Filed: Jan. 10, 2021

(65) Prior Publication Data
US 2022/0218901 A1    Jul. 14, 2022

(51) Int. Cl.
*A61M 5/168* (2006.01)

(52) U.S. Cl.
CPC ...... *A61M 5/1689* (2013.01); *A61M 5/16877* (2013.01); *A61M 2205/3306* (2013.01)

(58) Field of Classification Search
CPC ............ A61M 5/1689; A61M 5/16877; A61M 5/1411; A61M 5/168
See application file for complete search history.

(56) References Cited

U.S. PATENT DOCUMENTS

| | | | |
|---|---|---|---|
| 3,844,283 A * | 10/1974 | Dabney | A61M 5/1411 604/246 |
| 3,886,937 A | 6/1975 | Bobo | |
| 4,292,969 A * | 10/1981 | Raible | A61M 39/28 604/250 |
| 6,083,204 A | 7/2000 | Malerba | |
| 8,372,045 B2 | 2/2013 | Needle | |
| 9,855,387 B2 | 1/2018 | Small | |
| 2012/0123257 A1 | 5/2012 | Stokes, Jr. | |
| 2012/0283630 A1 * | 11/2012 | Lee | A61M 5/16886 604/65 |

(Continued)

FOREIGN PATENT DOCUMENTS

| | | |
|---|---|---|
| CN | 103347552 A | 10/2013 |
| CN | 104888306 A | 9/2015 |
| WO | 2020046889 A1 | 3/2020 |

OTHER PUBLICATIONS

"International Search Report" dated Mar. 24, 2020 for International application No. PCT/US2022/011741, International filing date Jan. 9, 2022.

*Primary Examiner* — Dung T Ulsh
(74) *Attorney, Agent, or Firm* — Winston Hsu

(57) ABSTRACT

An infusion set of a system for detecting and controlling drip rate is disclosed. The infusion set includes an infusion device and an adjustment device. The adjustment device is installed on the infusion device and for adjusting drip rate of injection in the infusion device. The infusion set of the system further includes an activating unit and at least one detecting module. The activating unit is coupled to a control unit of the system for providing staff in the hospital to control the drip rate through operation of the control unit. Further, the infusion set of the system further includes further includes at least one detecting module for drip counts, whereby it provides the staff with further information when controlling the drip rate of the infusion set.

16 Claims, 12 Drawing Sheets

(56) References Cited

U.S. PATENT DOCUMENTS

2013/0245439 A1    9/2013  Small
2016/0287785 A1*  10/2016  Isaacson ........... A61M 5/16881
2018/0193559 A1*   7/2018  Hirata ................... G01F 23/292

* cited by examiner

INFUSION SET WITH CAPABILITY OF CONTROLLING QUANTITY OF AN INJECTION INFUSED TO A LIMB AND SYSTEM FOR DETECTING AND CONTROLLING DRIP RATE OF AN INFUSION DEVICE

BACKGROUND OF THE INVENTION

1. Field of the Invention

The disclosure relates to an infusion set and a system, and more particularly, to an infusion set with capability of controlling quantity of an injection infused to a limb and a system for detecting and controlling drip rate of an infusion device.

2. Description of the Prior Art

Intravenous infusion is a route of administration often used to treat patients. Generally speaking, an infusion adjustment device is attached to the intravenous infusion set to adjust the quantity of infusion. Because the above-mentioned infusion adjustment device requires medical staff to observe the number of drops based on experience and then to manually operate the infusion adjusting device for adjustment of the infusion volume. Therefore, the conventional solution requires long-term training for medical staff, and cannot automatically adjust the drip rate for the patients based on the current drip rate of the injection. Accordingly, based on the responsibility and mission of the patient's health, it is indeed necessary to improve the drawbacks of the aforementioned intravenous infusion set.

SUMMARY OF THE INVENTION

For solving above drawbacks, the present disclosure provides an infusion set with capability of automatically controlling quantity of an injection and a system for detecting and controlling drip rate of an infusion device.

One embodiment of the present disclosure discloses an infusion set with capability of automatically controlling quantity of an injection. The infusion set includes an infusion device and an adjustment device. The infusion device includes a syringe body, an upper infusion tube, a lower infusion tube and an air tube. The syringe body has an inner chamber formed therein, and the inner chamber is configured to contain the injection. The upper infusion tube connects a side of the syringe body with an infusion member, and the injection drips from the infusion member to the inner chamber of the syringe body via the upper infusion tube. The lower infusion tube is connected to another side of the syringe body and configured to be connected to the limb. The air tube is connected to the side of the syringe body and configured to allow the injection contained in the inner chamber of the syringe body to be infused to the limb via the lower infusion tube. The adjustment device is installed on at least one of the upper infusion tube, the lower infusion tube and the air tube. The adjustment device includes a base and a movable member. The base is disposed on a side of the at least one of the upper infusion tube, the lower infusion tube and the air tube. The movable member is disposed on another side of the at least one of the upper infusion tube, the lower infusion tube and the air tube. The movable member is movable relative to the base, so as to deform a wall of the at least one of the upper infusion tube, the lower infusion tube and the air tube in cooperation with the base.

One embodiment of the present disclosure discloses a system for detecting and controlling drip rate of an infusion device. The system includes the infusion set as mentioned above, an activating unit and a control unit. The infusion set further includes a first detecting module including a first detecting module disposed aside the syringe body and configured to detect counts of the injection dripping from the infusion member to the inner chamber of the syringe body. The first detecting module includes a first light emitting unit and a first light receiving unit. The first light emitting unit is disposed on a side of the syringe body, and the first light emitting unit emits a light to the syringe body in a first light path through a first dripping path along which the injection drips from the infusion member to the inner chamber of the syringe body. The first light receiving unit is disposed on another side of the syringe body. The activating unit is coupled to the movable member of the adjustment device. The first detecting module is disposed aside the syringe body and configured to detect counts of the injection dripping from the infusion member to the inner chamber of the syringe body. The control unit is coupled to the activating unit and the first detecting module, and the control unit controls the activating unit to drive the movable member to move relative to the base based on the counts of the injection drips from the infusion member to the inner chamber of the syringe body.

One embodiment of the present disclosure discloses a system for detecting and controlling drip rate of an infusion device. The system includes the infusion set as mentioned above, wherein the syringe body includes a main portion and an auxiliary portion connected to the main portion, the inner chamber is formed in the main portion, the auxiliary portion has a liquid storage space formed therein, and the liquid storage space is communicated with the inner chamber, such that the injection in the inner chamber is dripped into the liquid storage space. The infusion set further includes a second detecting module disposed aside the auxiliary portion and configured to detect counts of the injection dripping from the inner chamber of the main portion to the liquid storage space of the auxiliary portion. The second detecting module includes a second light emitting unit and a second light receiving unit. The second light emitting unit is disposed on a side of the auxiliary portion, and the second light emitting unit emits a light to the auxiliary portion in a second light path through a second dripping path along which the injection drips from the inner chamber of the main portion to the liquid storage space of the auxiliary portion. The second light receiving unit is disposed on another side of the auxiliary portion.

In summary, the infusion set of the system for detecting and controlling drip rate of the infusion device of the disclosure includes the activating unit which is coupled to the movable member of the adjustment device and drives the movable member to move relative to the base, so as to deform the wall of the at least one of the upper infusion tube, the lower infusion tube and the air tube in cooperation with the base. In such a manner, the drip rate of the injection is able to be automatically adjusted by the activating module.

These and other objectives of the present disclosure will no doubt become obvious to those of ordinary skill in the art after reading the following detailed description of the preferred embodiment that is illustrated in the various figures and drawings.

DETAILED DESCRIPTION

Figure 1:
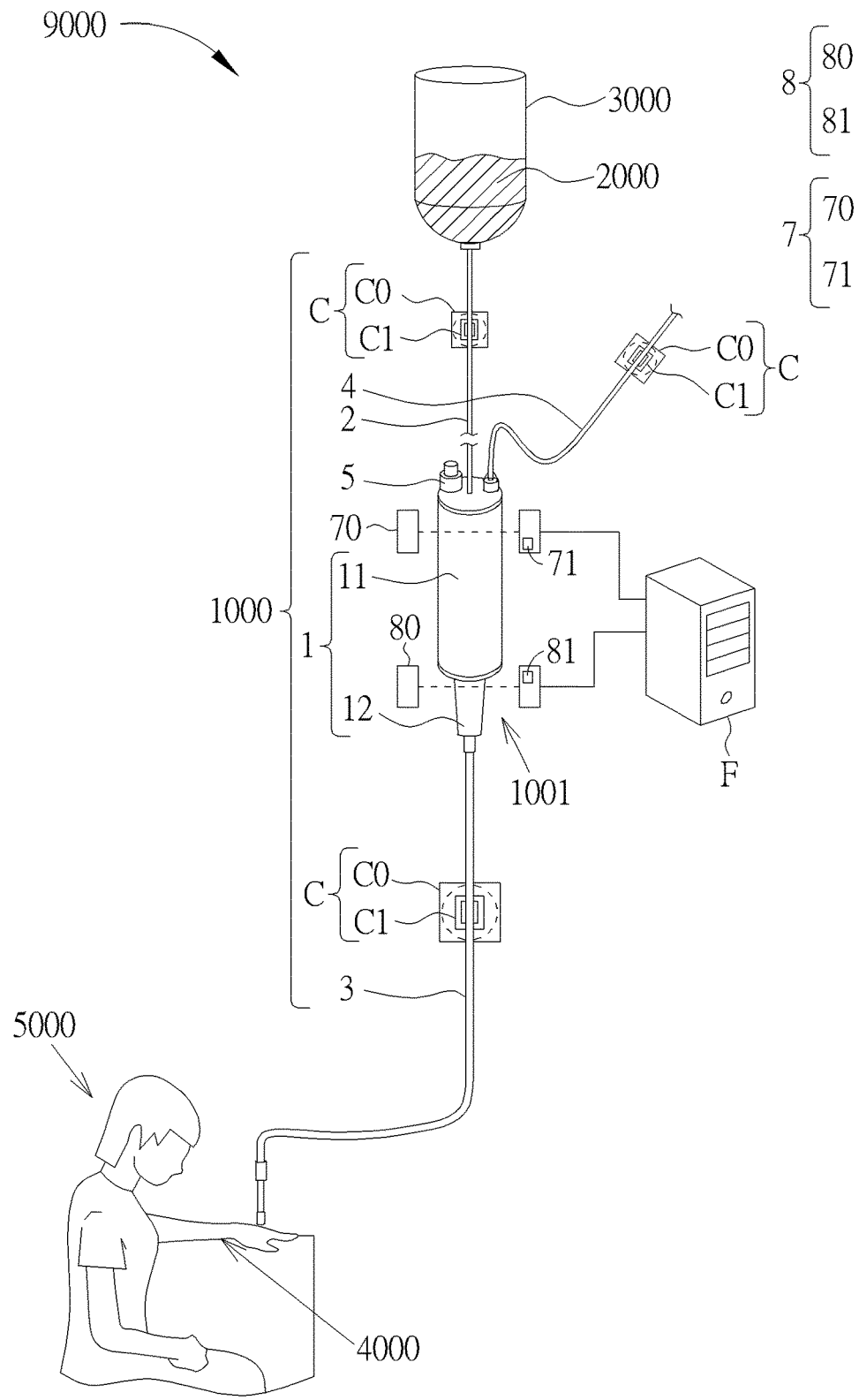
FIG. 1 is a diagram illustrating a system according to a first embodiment of the present disclosure.

In order to enable the skilled persons in the art to better understand the present disclosure, hereinafter preferred embodiments with drawings are provided for illustrating the present disclosure and the effect to be achieved. It should be noted that the drawings are simplified schematic diagrams. Therefore, only elements related to the present disclosure and combination relationship thereof are shown to provide a clearer description of the basic framework or implementation methods of the present disclosure. The actual elements and configuration may be more complicated. In addition, for the sake of convenience, the number of the components in the drawings could be unequal the actual number thereof, the shape and size of the components may not draw in proportion to the actual shape and size, and the proportion thereof can be adjusted according to design requirements.

The directional terminology in the following embodiments, such as top, bottom, left, right, front or back, is used with reference to the orientation of the Figure(s) being described. As such, the directional terminology is used for purposes of illustration and is in no way limiting.

The ordinal number terminology, such as first, second and third, can be used to describe various elements, and the elements are not limited by definition of the ordinal number terminology. The ordinal number terminology is used to distinguish one element from other elements in the specification, and the ordinal number terminology of the element in the claims is arranged according to the claimed order and could be different from that in the specification. As such, a first element recited in the following description could be a second element in the claims.

Please refer to FIG. 1. FIG. 1 is a diagram illustrating a system 9000 according to a first embodiment of the present disclosure. The system 9000 includes an infusion set 1000. The infusion set 1000 includes an infusion device 1001 which includes a syringe body 1, an upper infusion tube 2, a lower infusion tube 3 and an air tube 4. The syringe body 1 has an inner chamber 10 formed therein (the inner chamber 10 can be seen in FIG. 6), and the inner chamber 10 is configured to contain an injection 2000.

The upper infusion tube 2 connects a side of the syringe body 1 with an infusion member 3000, such that an injection 2000 in the infusion member 3000 drips from the infusion member 3000 to the inner chamber 10 of the syringe body 1 via the upper infusion tube 2. The lower infusion tube 3 is connected to another side of the syringe body 1 and configured to be connected to a limb 4000 of a person 5000. The air tube 4 is connected to the side of the syringe body 1 and configured to allow the injection 2000 contained in the inner chamber 10 of the syringe body 1 to be infused to the limb 4000 via the lower infusion tube 3.

In practical application, the infusion device 1001 can include an injection port 5. The infusion member 3000 can be an infusion bag, and the injection 2000 contained in the infusion bag can be intravenous fluid, such as intravenous antibiotics, normal saline, glucose solution, etc.

Furthermore, the infusion set 1000 includes an adjustment device C installed on at least one of the upper infusion tube 2, the lower infusion tube 3 and the air tube 4. The adjustment device C includes a base C0 and a movable member C1. The base C0 is disposed on a side of the at least one of the upper infusion tube 2, the lower infusion tube 3 and the air tube 4. The movable member C1 is disposed on another side of the at least one of the upper infusion tube 2, the lower infusion tube 3 and the air tube 4. The movable member C1 is movable relative to the base C0, so as to deform a wall of the at least one of the upper infusion tube 2, the lower infusion tube 3 and the air tube 4 in cooperation with the base C0.

In such a manner, movement of the movable member C1 relative to the base C0 results in deformation of the wall of the at least one of the upper infusion tube 2, the lower infusion tube 3 and the air tube 4, which enables the infusion set 1000 to adjust and control the quantity of the injection 2000 infused to the limb 4000 of the person 5000.

Figure 2:
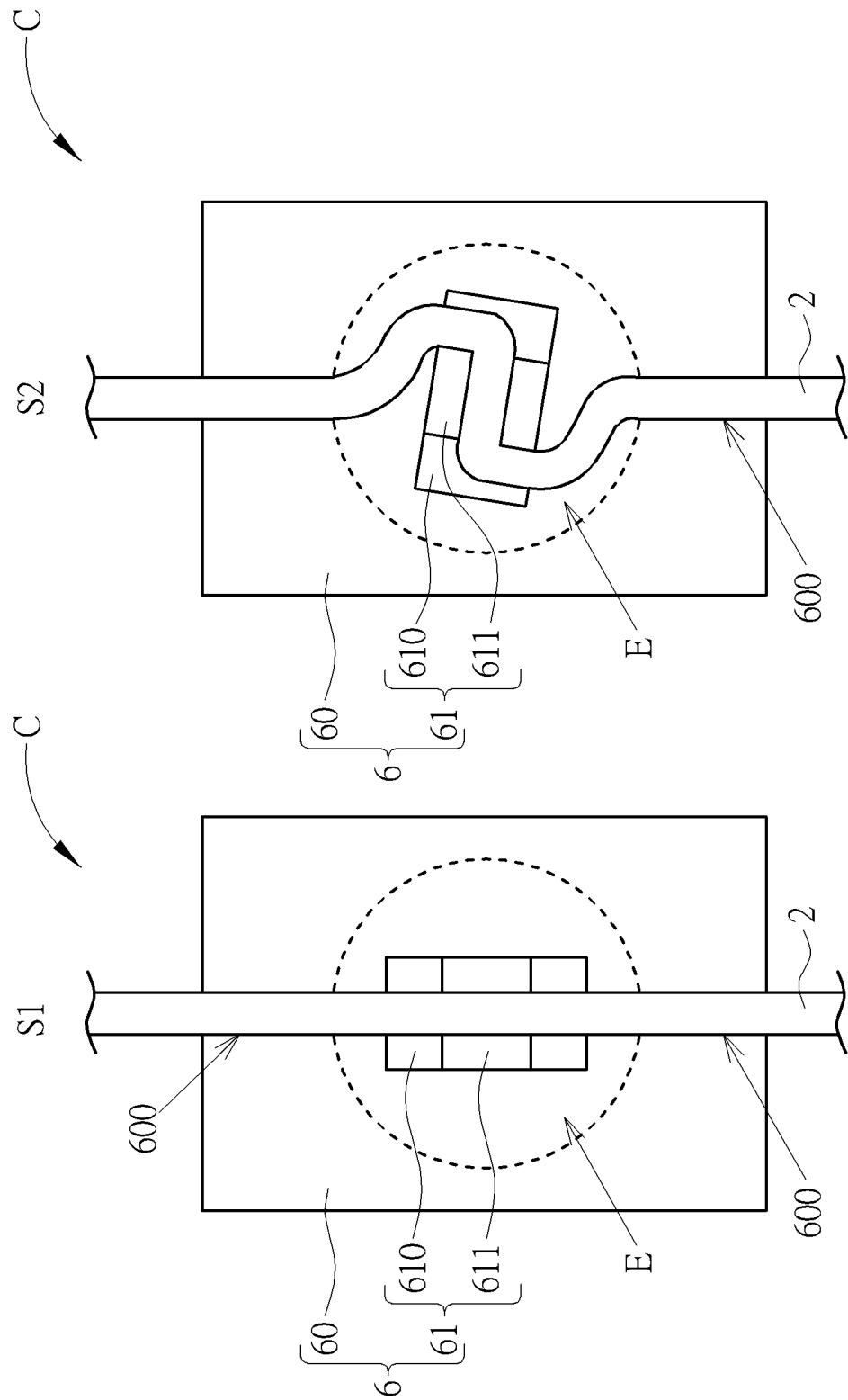
FIG. 2 is a diagram illustrating an adjustment device in a release state and in a twisting state according to the first embodiment of the present disclosure.
Figure 3:
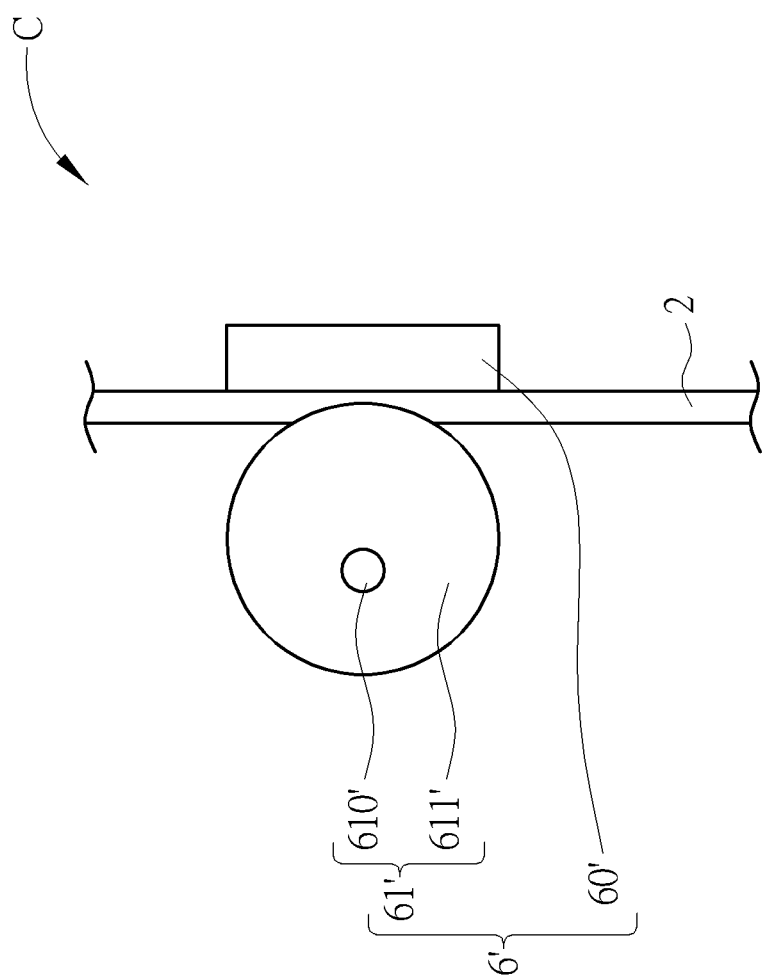
FIG. 3 is a diagram illustrating the adjustment device according to another embodiment of the present disclosure.
Figure 4:
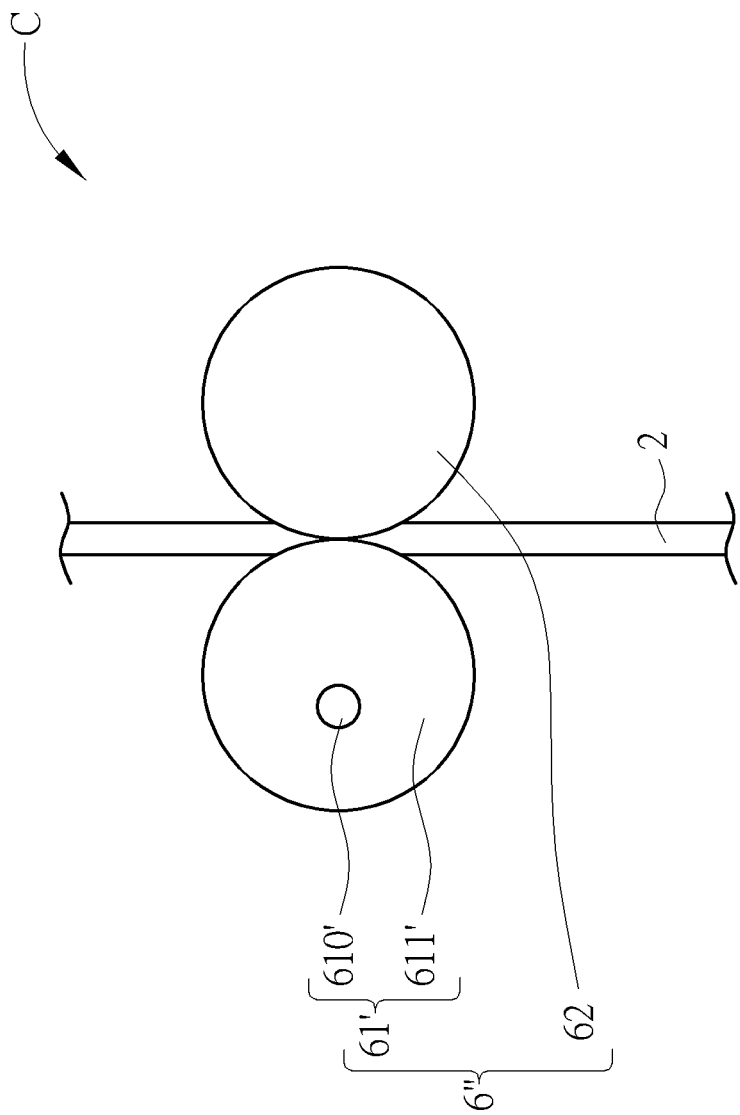
FIG. 4 is a diagram illustrating the adjustment device according to yet another embodiment of the present disclosure.
Figure 5:
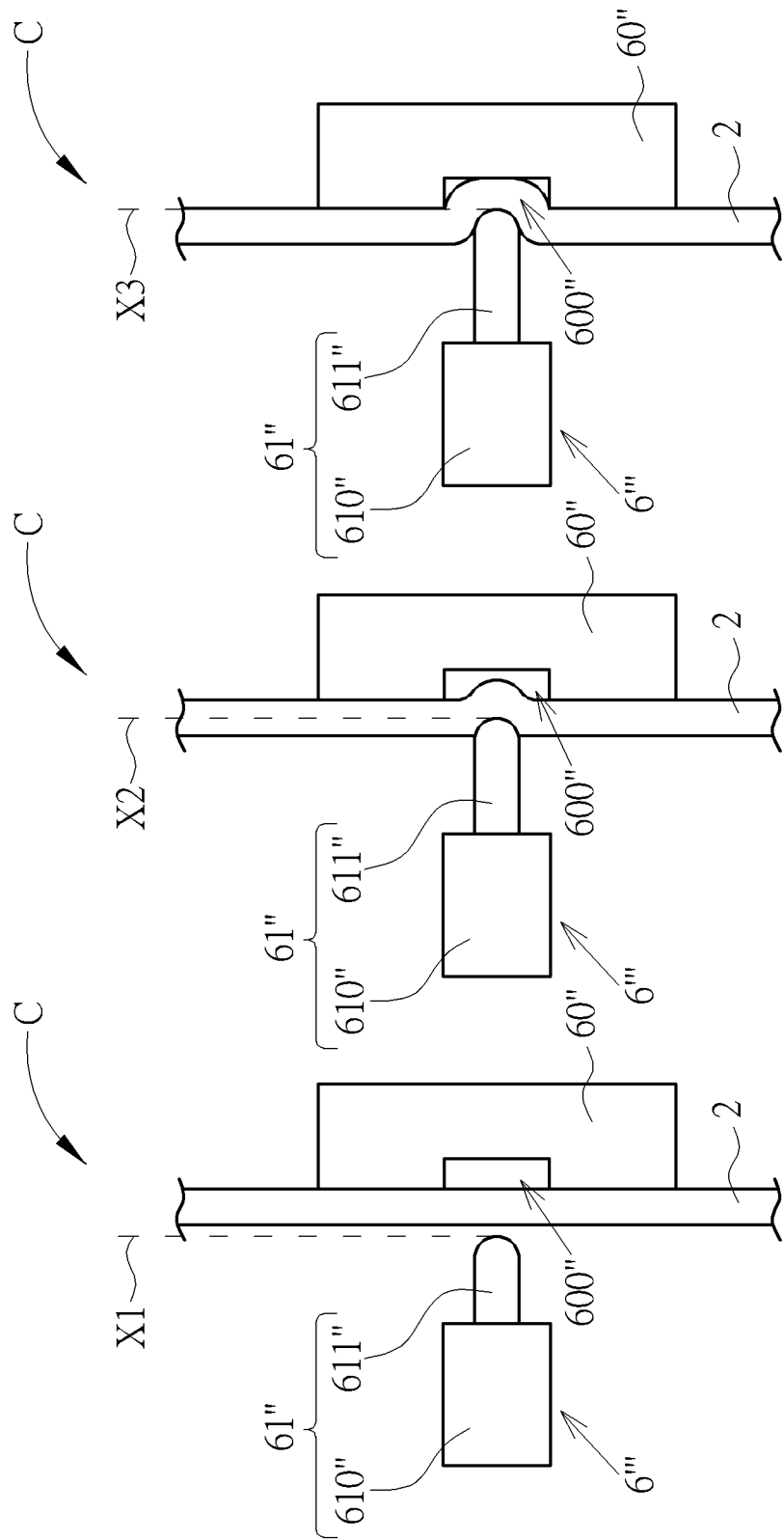
FIG. 5 is a diagram illustrating the adjustment device according to yet another embodiment of the present disclosure.

Please refer to FIG. 1 to FIG. 5. FIG. 2 is a diagram illustrating the adjustment device C in a release state S1 and in a twisting state S2 according to the first embodiment of the present disclosure. FIG. 3 is a diagram illustrating the adjustment device C according to another embodiment of the present disclosure. FIG. 4 is a diagram illustrating the adjustment device C according to yet another embodiment of the present disclosure. FIG. 5 is a diagram illustrating the adjustment device C according to yet another embodiment of the present disclosure. It is noticed that FIG. 2 to FIG. 5 show four embodiments of mechanisms for illustrating the adjustment device C, any of which can be adapted to the at least one of the upper infusion tube 2, the lower infusion tube 3 and the air tube 4. Further, identical components with denoted in these embodiments have identical structures and functions, and further description is omitted for simplicity.

As shown in FIG. 2, the adjustment device C is a button set 6, the base is a mounting member 60, and the movable member is a rotating button 61 rotatable relative to the mounting member 60. The mounting member 60 has a channel 600 formed therethrough to be mounted with the the upper infusion tube 2. The rotating button 61 includes a button body 610 and a pair of tabs 611. The button body 610 mounted with the mounting member 60 in a rotatable manner. The pair of tabs 611 protrude from the button body 610 and are rotatable with the button body 610. The pair of tabs 611 engage with the upper infusion tube 2, so as to twist the wall of the upper infusion tube 2 in cooperation with the mounting member 60 through rotation of the button body 610 relative to the mounting member 60.

As shown in FIG. 1 and FIG. 2, the infusion set 1000 can further include an activating unit C and the system 9000 can further include a control unit F. In the present disclosure, the activating unit C can be a stepping motor or a servo motor which is coupled to the button body 610 and the control unit F. The control unit F is configured to generate a control signal for controlling the activating unit C to rotate the button body 610. When the button body 610 is rotated, the button body 610 will twist the wall of the upper infusion tube 2 due to engagement of the pair of tabs 611 with the wall of the upper infusion tube 2, so as to vary section of the upper infusion tube 2.

In the present disclosure, the control unit F can be a server, a desktop computer, etc., and provided the hospital staff to operate to generate the control signal. In such a manner, the hospital staff is able to control drip rate of the infusion device 1001 of the infusion set 1000 through operation of the control unit F.

As shown in FIG. 3, the adjustment device C is a cam set 6', the base is a secure member 60', and the movable member is a rotating cam 61' rotatable relative to the secure member 60'. The rotating cam 61' includes an axis 610' and a cam body 611'. The axis 610' is disposed on a side of the upper infusion tube 2. The cam body 611' is eccentrically mounted with the axis 610'. The cam body 611' presses the wall of the upper infusion tube 2 through rotation of the cam body 611' relative to the secure member 60', so as to vary section of the upper infusion tube 2.

As shown in FIG. 4, the adjustment device C is a cam set 6'', and the major difference between the cam set 6'' shown in FIG. 4 and the cam set 6' shown in FIG. 3 is that the base of the cam set 6'' is a secure cam 62 instead of secure member.

As shown in FIG. 5, the adjustment device C is a cylinder set 6''', the base is a holding member 60'', and the movable member is a cylinder device 61''. The cylinder device 61'' includes a cylinder housing 610'' and a cylinder head 611''. The cylinder housing 610'' is disposed on a side of the upper infusion tube 2. The cylinder head 611'' is stretchable relative to the cylinder housing 610''. The cylinder head 611'' presses the wall of the upper infusion tube 2 through the cylinder head 611'' stretching out from the cylinder housing 610'', so as to vary section of the upper infusion tube 2.

Figure 6:
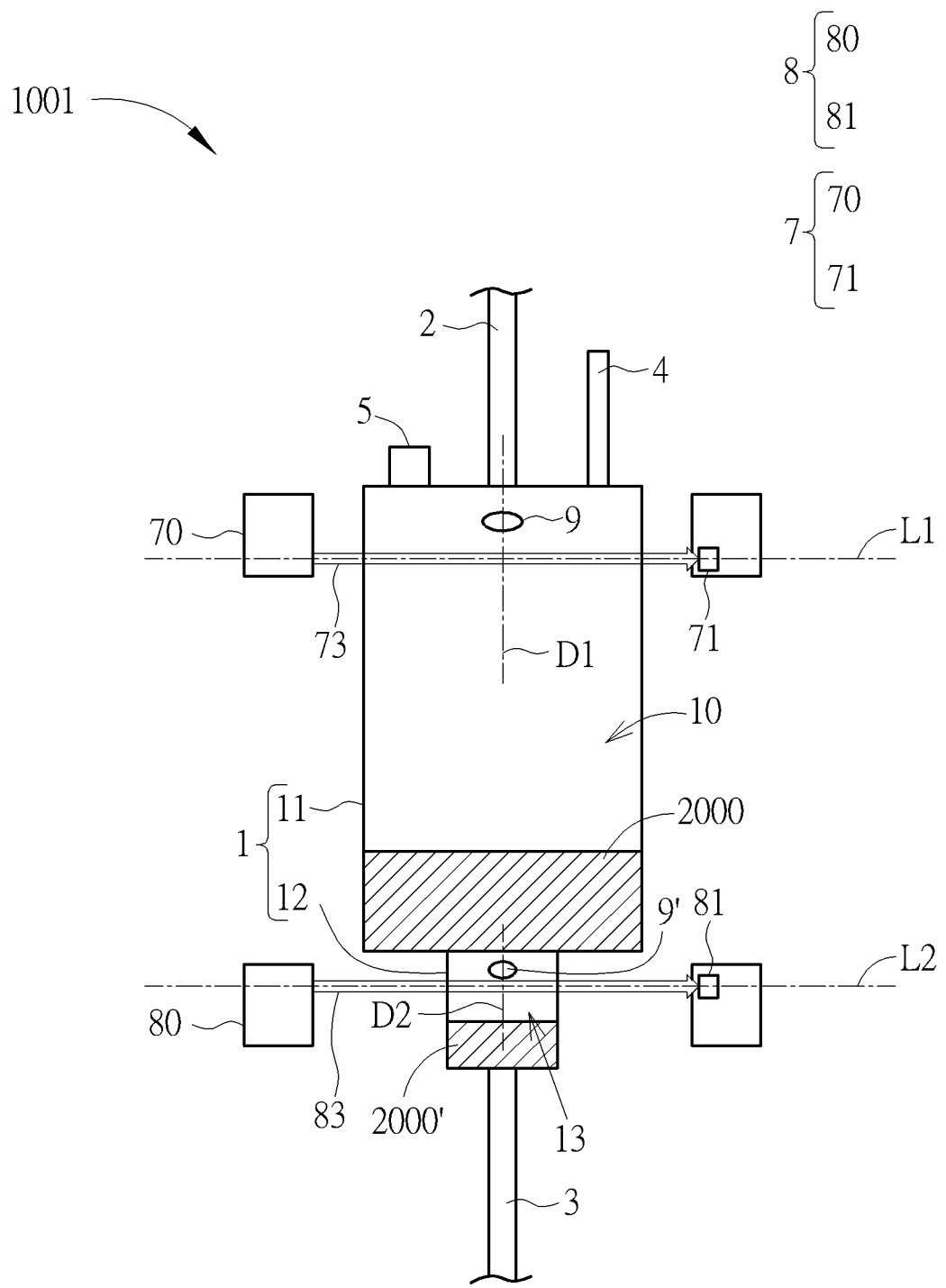
FIG. 6 is a diagram illustrating an infusion device in a non-interrupting state according to the first embodiment of the present disclosure.
Figure 7:
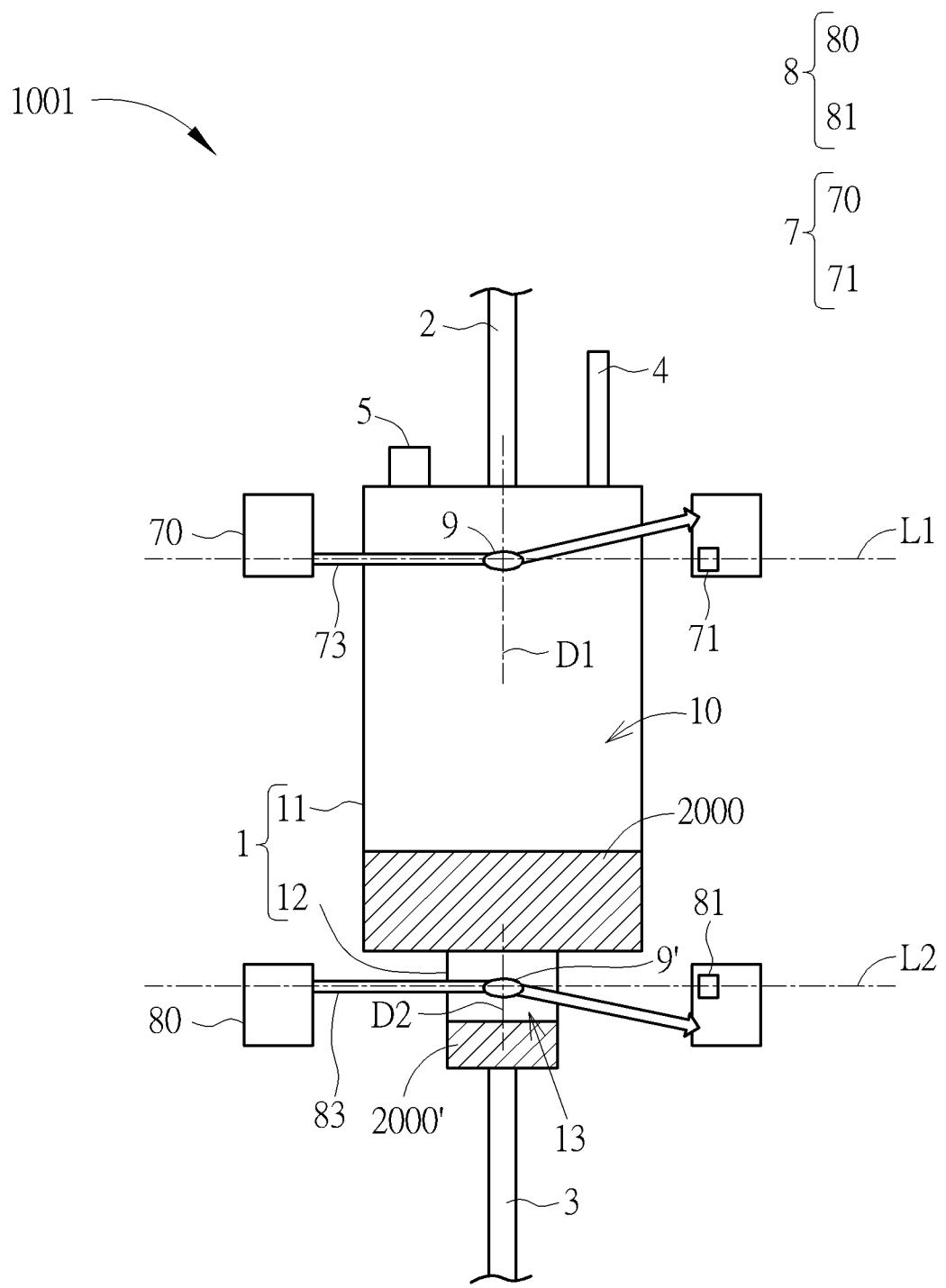
FIG. 7 is a diagram illustrating the infusion device in an interrupting state according to the first embodiment of the present disclosure.

Please refer to FIG. 1, FIG. 6 and FIG. 7. FIG. 6 is a diagram illustrating part of the infusion device 1001 in a non-interrupting state according to the first embodiment of the present disclosure. FIG. 7 is a diagram illustrating part of the infusion device 1001 in an interrupting state according to the first embodiment of the present disclosure. As shown in FIG. 1, FIG. 6 and FIG. 7, the infusion set 1000 further includes a first detecting module 7. The first detecting module 7 is disposed aside the syringe body 1 and includes a first light emitting unit 70 and a first light receiving unit 71.

The first light emitting unit 70 is disposed on a side of the syringe body 1, and the first light emitting unit 70 emits a light 73 to the syringe body 1 in a first light path L1 through a first dripping path D1 along which the injection 2000 drips from the infusion member 3000 to the inner chamber 10 of the syringe body 1. The first light receiving unit 71 is disposed on another side of the syringe body 1. In the present disclosure, the first detecting module 7 can be an infrared sensor module, but the present disclosure is not limited thereto.

As shown in FIG. 6, when a drip 9 of the injection 2000 on the first dripping path D1 does not interrupt the light 73 in the first light path L1, the light 73 is not refracted by the drip 9, and the light 73 passes in the first light path L1, such that the first light receiving unit 71 receives the light 73 emitted from the first light emitting unit 70 and generates a first light strength signal accordingly. As shown in FIG. 7, when the drip 9 of the injection 2000 on the first dripping path D1 interrupts the light 73 in the first light path L1, the light 73 is refracted away from the first light path L1 by the drip 9, such that the first light receiving unit 71 does not receive the light 73 emitted from the first light emitting unit 70 and generates a second light strength signal accordingly.

Furthermore, the first detecting module 7 is coupled to the control unit F, such that the control unit F processes the first light strength signal and/or the second light strength signal for rendering counts of the drip 9. For example, the control unit F renders one count of the drip 9 according to the first light strength signal or the second light strength signal received. Alternatively, the control unit F renders one count of the drip 9 as well according to a combination of the first light strength signal and the second light strength signal. In other words, the first light strength signal, the second light strength signal or a combination thereof is rendered one count of the drip 9 of the injection 2000 on the first dripping path D1.

As shown in FIG. 6 and FIG. 7, the syringe body 1 includes a main portion 11 and an auxiliary portion 12 connected to the main portion 11. The inner chamber 10 is formed in the main portion 11, and the first detecting module 7 is disposed aside the main portion 11. The auxiliary portion 12 has a liquid storage space 13 formed therein. The liquid storage space 13 is communicated with the inner chamber 10, such that the injection 2000 in the inner chamber 10 is dripped into the liquid storage space 13.

It is noticed that the infusion set 1000 with the first detecting module 7 disposed aside the main portion 11 of the syringe body 1 is illustrated as an embodiment herein, but the present disclosure is not limited thereto. For example, in a second embodiment, the infusion set 1000 includes a second detecting module 8 disposed aside the auxiliary portion 12. The second detecting module 8 includes a second light emitting unit 80 and a second light receiving unit 81. The second light emitting unit 80 is disposed on a side of the auxiliary portion 12. The second light emitting unit 80 emits a light 83 to the auxiliary portion 12 in a second light path L2 through a second dripping path D2 along which the injection drips from the inner chamber 10 of the main portion 11 to the liquid storage space 13 of the auxiliary portion 12. The second light receiving unit 81 is disposed on another side of the auxiliary portion 12.

As shown in FIG. 6, when a drip 9' of the injection 2000 on the second dripping path D2 does not interrupt the light 83 in the second light path L2, the light 83 is not refracted by the drip 9', and the light 83 passes in the second light path L2, such that the second light receiving unit 81 receives the light 83 emitted from the second light emitting unit 80 and generates a third light strength signal accordingly. As shown in FIG. 7, when the drip 9' of the injection 2000 on the second dripping path D2 interrupts the light 83 in the second light path L2, the light 83 is refracted away from the second light path L2 by the drip 9', such that the second light receiving unit 81 does not receive the light 83 emitted from the second light emitting unit 80 and generates a fourth light strength signal accordingly.

Similarly, the second detecting module 8 is coupled to the control unit F, such that the control unit F processes the third light strength signal and/or the fourth light strength signal for rendering counts of the drip 9'. For example, the control unit F renders one count of the drip 9' according to the third light strength signal or the fourth light strength signal received. Alternatively, the control unit F renders one count of the drip 9' as well according to a combination of the third light strength signal and the fourth light strength signal. In other words, the third light strength signal, the fourth light strength signal or a combination thereof is rendered one count of the drip 9' of the injection 2000 on the second dripping path D2.

In summary, drip rate of the infusion set 1000 can be controlled by the adjustment device C in a manner of rotation of the rotating button 61, rotation of the rotating cam 61' or stretching of the cylinder head 611". Further, the infusion set 1000 includes detecting modules, such as the first detecting module 7 for detecting the counts of the drip 9 into the main portion 11 of the syringe body 1 and/or the counts of the drip 9' into the auxiliary portion 12 of the syringe body 1, and the control unit F coupled to the activating module E and the first detecting module 7 and/or the second detecting module 8. In such a manner, the control unit F of the system 9000 is able to control the activating module E to activate the activating module E to drive the adjustment device C in a manner of rotation of the rotating button 61, rotation of the rotating cam 61' or stretching of the cylinder head 611" based on the counts of the drip 9 into the main portion 11 of the syringe body 1 and/or the counts of the drip 9' into the auxiliary portion 12 of the syringe body 1.

Figure 8:
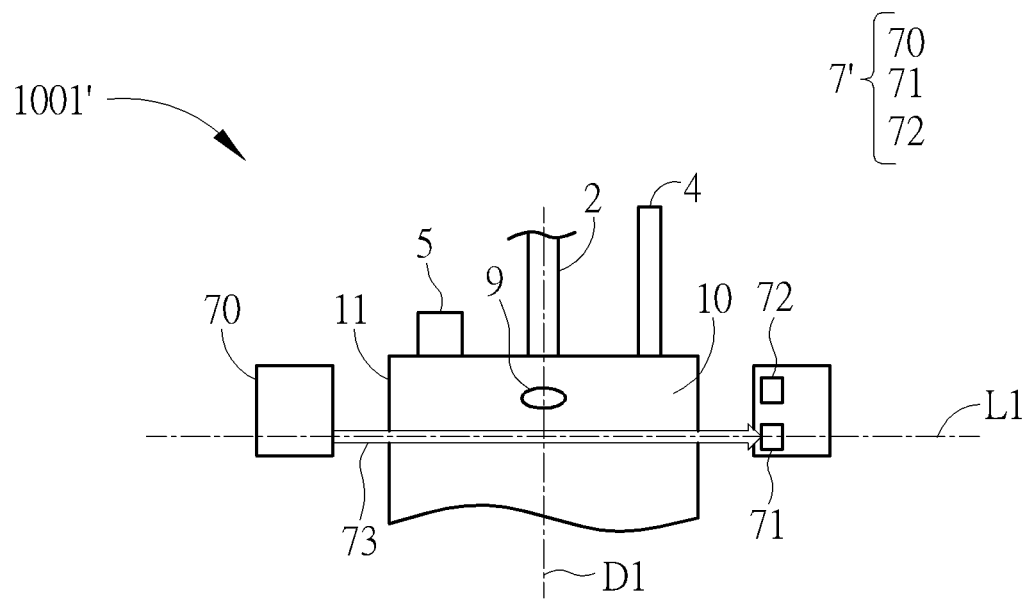
FIG. 8 is a diagram illustrating part of an infusion device in a non-interrupting state according to a third embodiment of the present disclosure.
Figure 9:
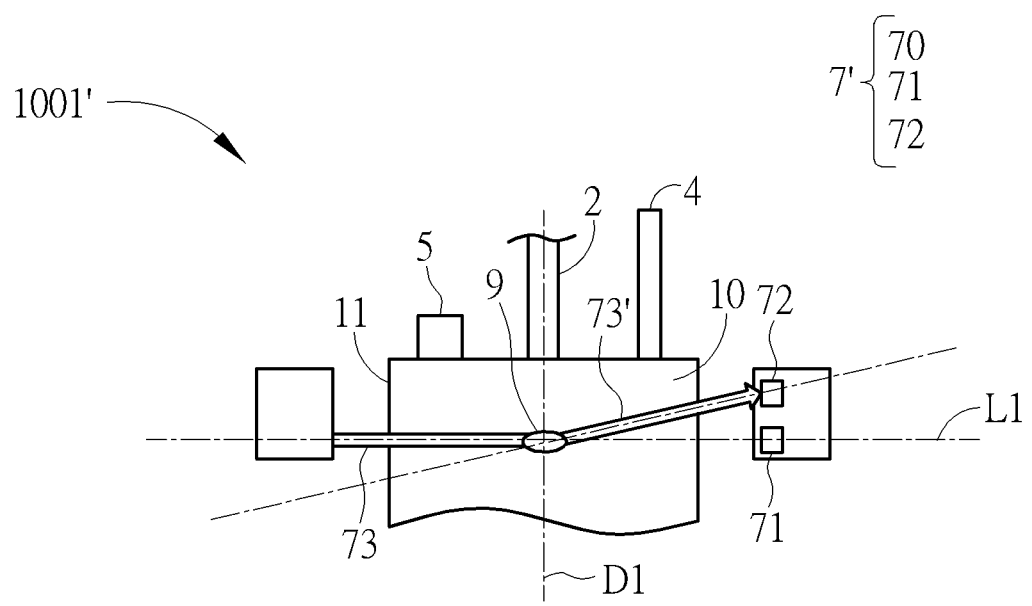
FIG. 9 is a diagram illustrating part of the infusion device in an interrupting state according to the third embodiment of the present disclosure.

Please refer to FIG. 8 and FIG. 9. FIG. 8 is a diagram illustrating part of an infusion device 1001' in a non-interrupting state according to a third embodiment of the present disclosure. FIG. 9 is a diagram illustrating part of the infusion device 1001' in an interrupting state according to the third embodiment of the present disclosure. The major difference between the infusion device 1001' and the infusion device 1001 is that a first detecting module 7' further includes a first auxiliary light receiving unit 72, and the first auxiliary light receiving unit 72 is disposed aside the first light receiving unit 71.

Figure 10:
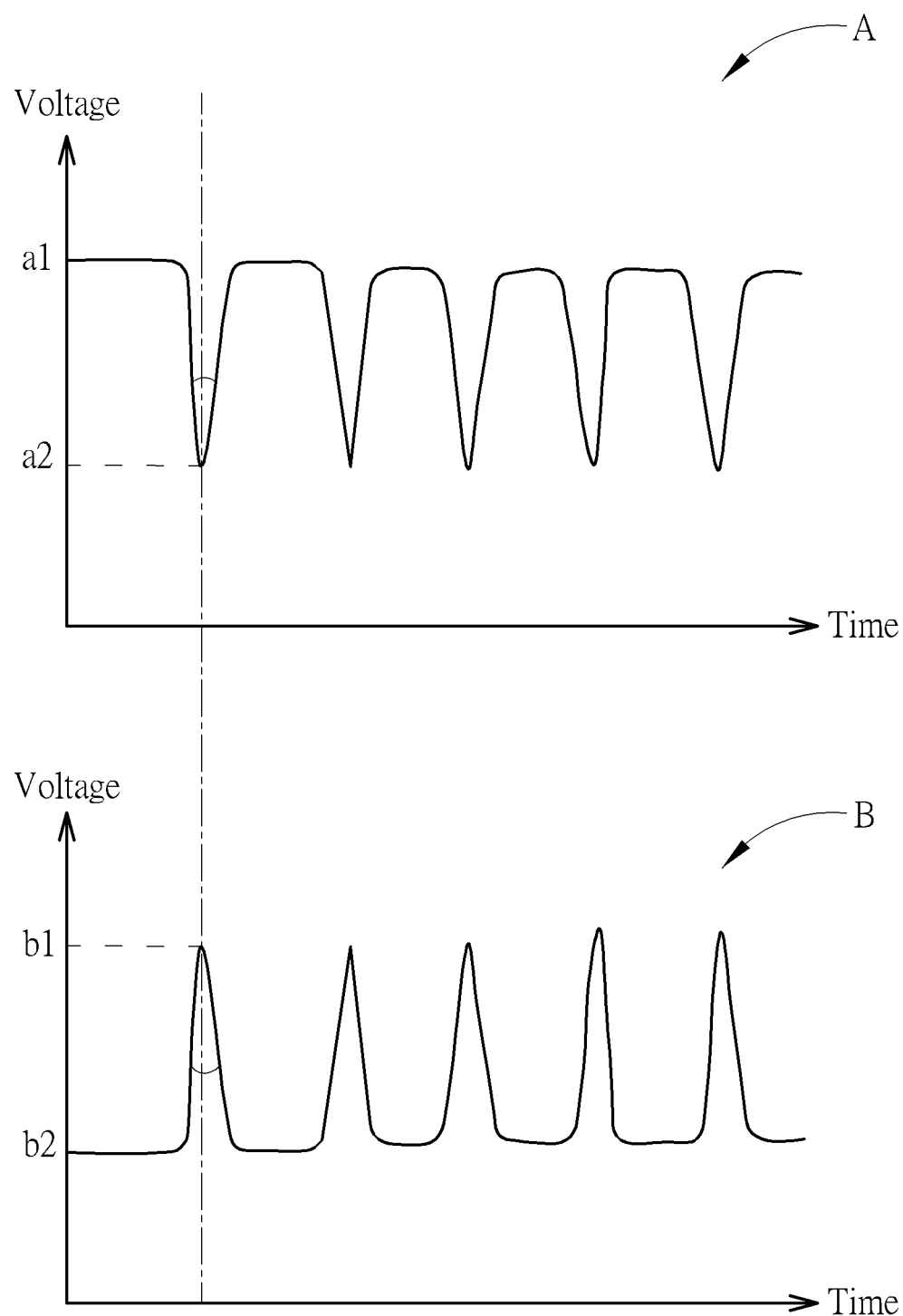
FIG. 10 is a diagram illustrating a first processing signal set generated by a first detecting module and a second processing signal set generated by a first auxiliary light receiving unit according to the third embodiment of the present disclosure.

Please refer to FIG. 10 as well. FIG. 10 is a diagram illustrating a first processing signal set A generated by the first detecting module 7' and a second processing signal set B generated by the first auxiliary light receiving unit 72 according to the third embodiment of the present disclosure. As shown in FIG. 8 and FIG. 10, when a drip 9 of the injection 2000 on a first dripping path D1 does not interrupt a light 73 in a first light path L1, the light 73 is not refracted by the drip 9, and the light 73 passes in the first light path L1, such that the first light receiving unit 71 receives the light 73 emitted from the first light emitting unit 70 and generates a first light strength signal a1, accordingly. In the meanwhile, the first auxiliary light receiving unit 72 does not receive the light 73 and generates a second auxiliary light strength signal b2, accordingly.

As shown in FIG. 9 and FIG. 10, when the drip 9 of the injection 2000 on the first dripping path D1 interrupts the light 73 in the first light path L1, the light 73 is refracted away from the first light path L1 by the drip 9, such that the first light receiving unit 71 does not receive the light 73 emitted from the first light emitting unit 70 and generates a second light strength signal a2, accordingly. In the meanwhile, the first auxiliary light receiving unit 72 receives the light 73 refracted by the drip 9 and generates a first auxiliary light strength signal b1, accordingly.

Furthermore, the first detecting module 7' is coupled to the control unit F, such that the control unit F processes the first processing signal set A and the second processing signal set B for rendering counts of the drip 9. For example, a coincidence of the second light strength signal a2 of the first processing signal set A and the first auxiliary light strength signal b1 of the second processing signal set B is rendered one count of the drip 9 of the injection 2000 on the first dripping path D1.

Figure 11:
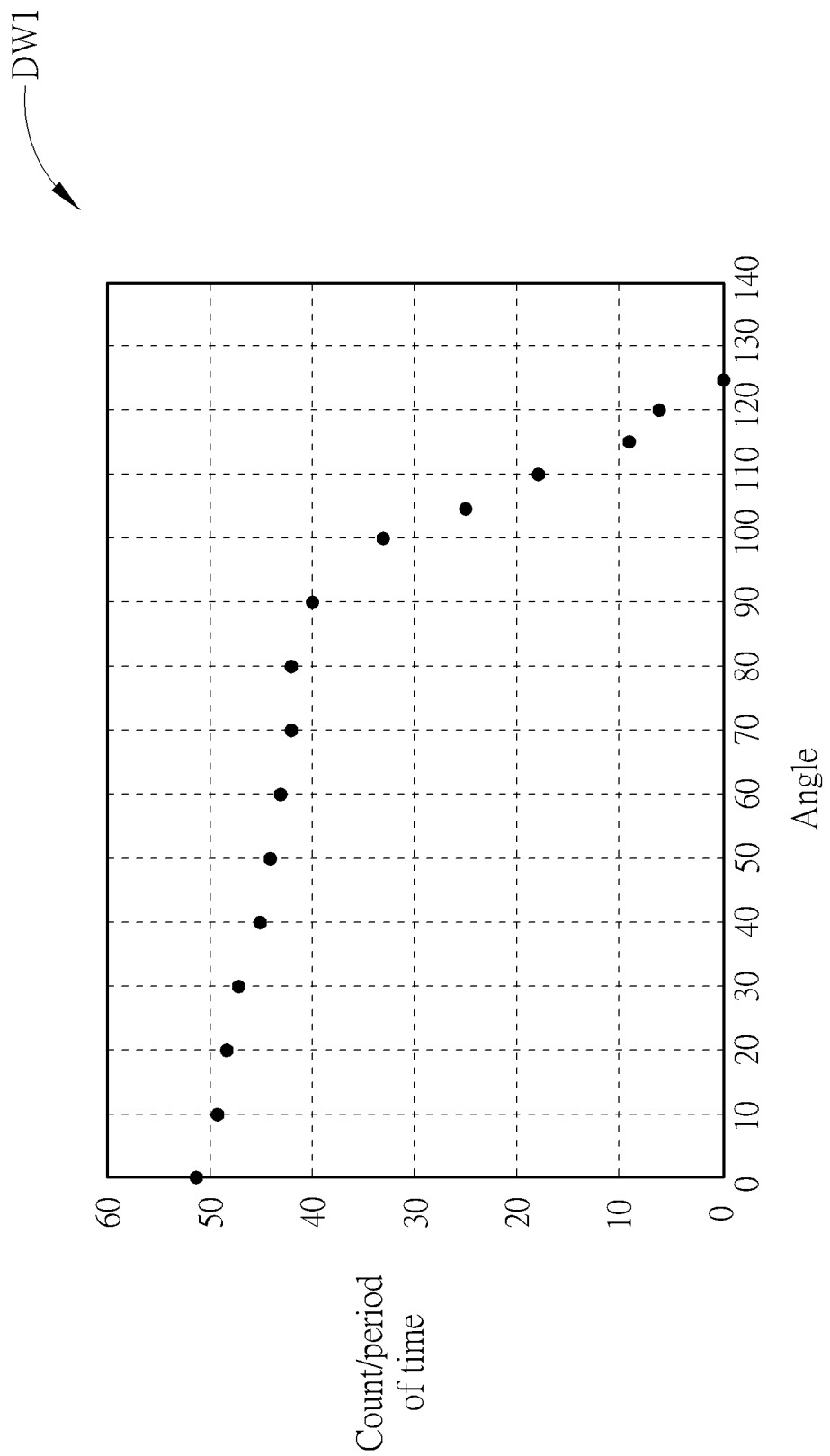
FIG. 11 is a first plot of angle versus count per period of time according to the third embodiment of the present disclosure.

Furthermore, referring to FIG. 11, FIG. 11 is a first plot of angle versus count per period of time DW1 according to the third embodiment of the present disclosure. As mentioned above, the present disclosure utilizes the adjustment device C to control drip rate of the infusion 2000, and the present disclosure further utilizes the first detecting module 7' to monitor the counts of the drip 9 of the injection 2000 on the first dripping path D1. As a result, it is able to construct the plot which is as shown in FIG. 11 and illustrates the angle by which the movement member C1 rotates versus the counts of the drip 9 of the injection 2000 on the first dripping path D1, so as to provide the staff in hospital with further information when controlling the drip rate of the infusion device 1001' of the infusion set 1000 through operation of the control unit F.

Figure 12:
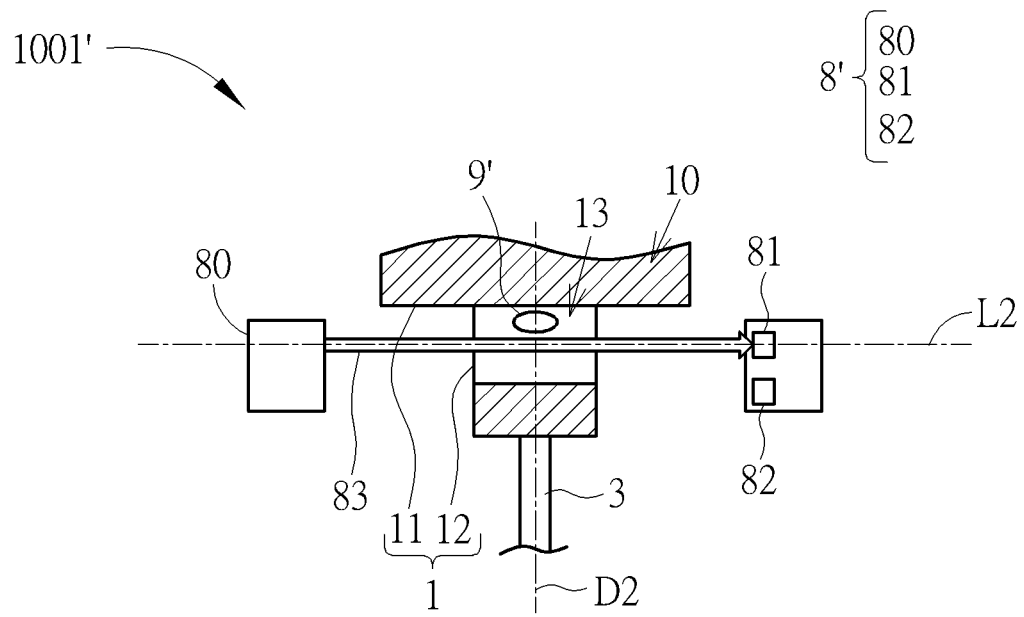
FIG. 12 is a diagram illustrating part of an infusion device 1001' in a non-interrupting state according to a fourth embodiment of the present disclosure.
Figure 13:
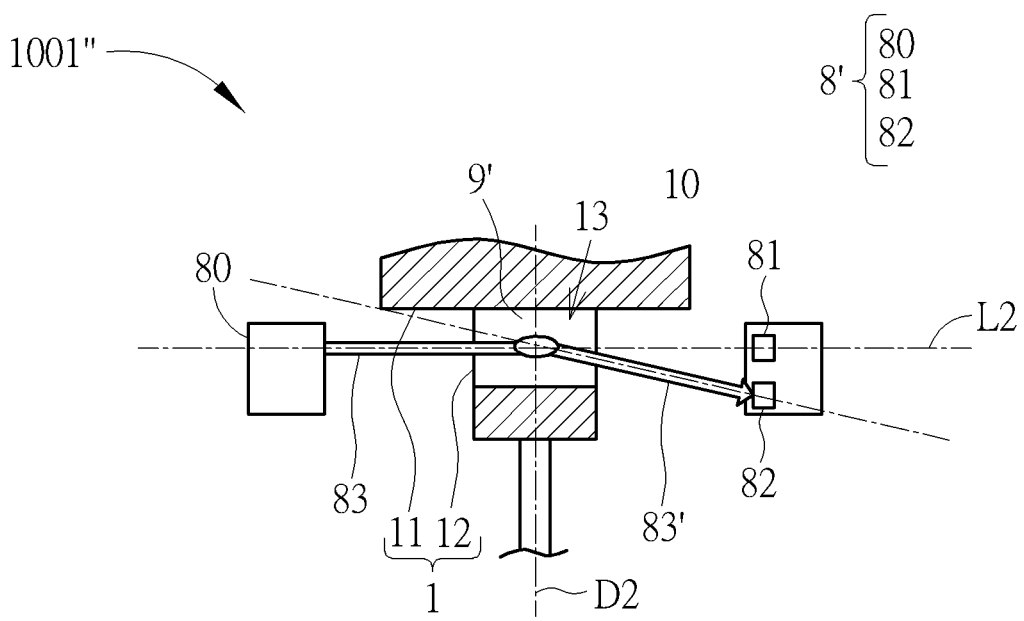
FIG. 13 is a diagram illustrating part of an infusion device in an interrupting state according to the fourth embodiment of the present disclosure.

Please refer to FIG. 12 and FIG. 13. FIG. 12 is a diagram illustrating part of an infusion device 1001' in a non-interrupting state according to a fourth embodiment of the present disclosure. FIG. 13 is a diagram illustrating part of the infusion device 1001' in an interrupting state according to the fourth embodiment of the present disclosure. The major difference between the infusion device 1001' and the infusion device 1001 is that a second detecting module 8' further includes a second auxiliary light receiving unit 82, and the second auxiliary light receiving unit 82 is disposed aside the second light receiving unit 81.

As shown in FIG. 12, when a drip 9' of the injection 2000 on a second dripping path D2 does not interrupt a light 83 in a second light path L2, the light 83 is not refracted by the drip 9', and the light 83 passes in the second light path L2, such that the second light receiving unit 81 receives the light 83 emitted from the second light emitting unit 80 and generates a third light strength signal, accordingly. In the meanwhile, the second auxiliary light receiving unit 82 does not receive the light 83 and generates a fourth auxiliary light strength signal, accordingly.

As shown in FIG. 13, when the drip 9' of the injection 2000 on the second dripping path D2 interrupts the light 83 in the second light path L2, the light 83 is refracted away from the second light path L2 by the drip 9', such that the second light receiving unit 81 does not receive the light 83 emitted from the second light emitting unit 80 and generates a fourth light strength signal, accordingly. In the meanwhile, the second auxiliary light receiving unit 82 receives the light 83 refracted by the drip 9' and generates a third auxiliary light strength signal, accordingly.

Furthermore, the second detecting module 8' is coupled to the control unit F, such that the control unit F processes a third processing signal set including the third light strength signal and the fourth light strength signal and a second processing signal set for rendering counts of the drip 9'. For example, a coincidence of the fourth light strength signal of the third processing signal set and the second auxiliary light strength signal of the fourth processing signal set is rendered one count of the drip 9' of the injection 2000 on the second dripping path D2.

Figure 14:
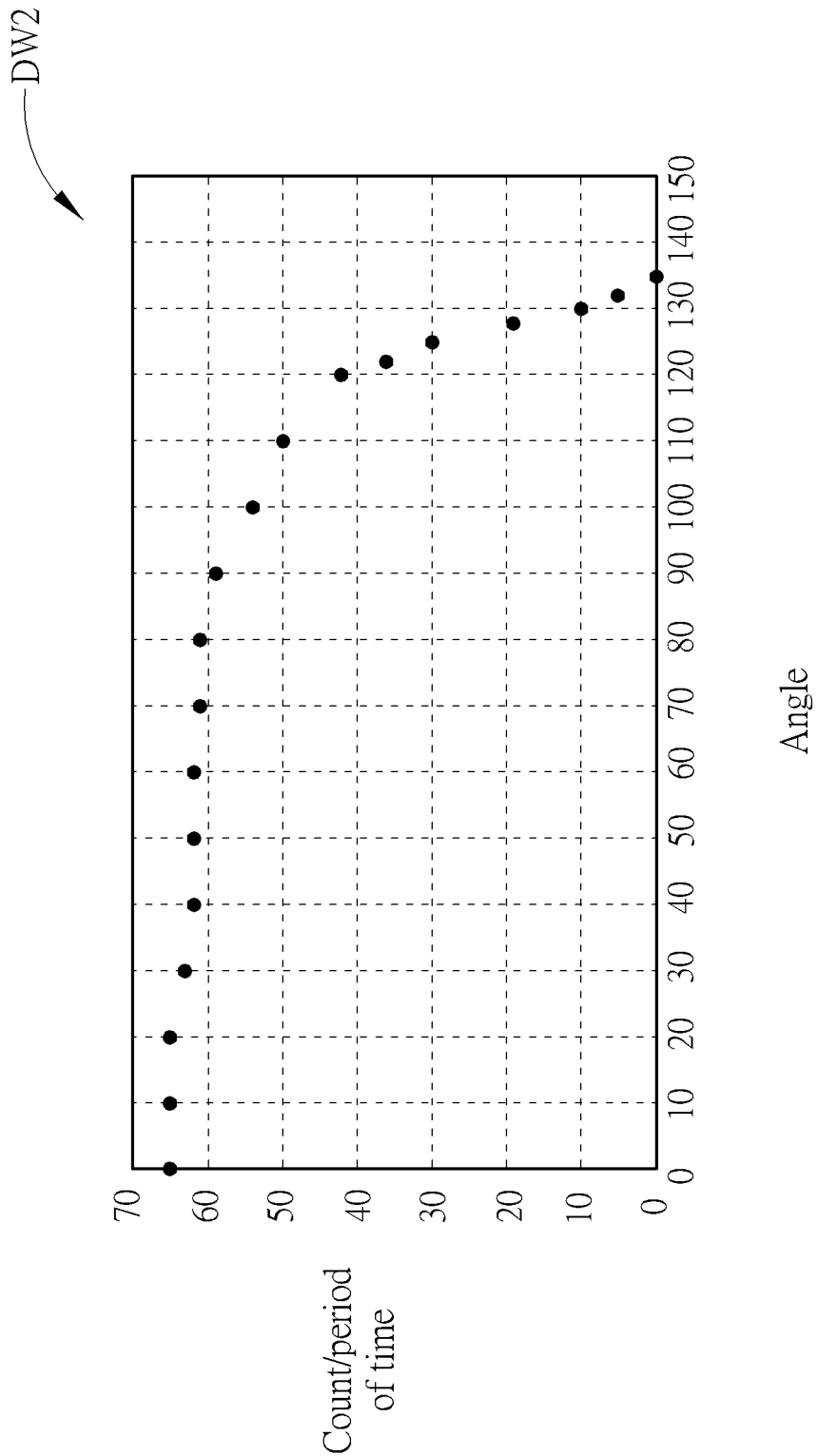
FIG. 14 is a second plot of angle versus count per period of time according to the fourth embodiment of the present disclosure.

Furthermore, referring to FIG. 14, FIG. 14 is a second plot of angle versus count per period of time DW2 according to the fourth embodiment of the present disclosure. As mentioned above, the present disclosure utilizes the adjustment device C to control drip rate of the infusion 2000, and the present disclosure further utilizes the second detecting module 8' to monitor the counts of the drip 9' of the injection 2000 on the second dripping path D2. As a result, it is able to construct the plot which is as shown in FIG. 14 and illustrates the angle by which the movement member C1 rotates versus the counts of the drip 9' of the injection 2000 on the second dripping path D2, so as to provide the staff in hospital with further information when controlling the drip rate of the infusion device 1001" of the infusion set 1000 through operation of the control unit F.

Compared to the prior art, the infusion set of the system for detecting and controlling drip rate of the infusion device of the disclosure includes the activating unit which is coupled to the movable member of the adjustment device and drives the movable member to move relative to the base, so as to deform the wall of the at least one of the upper infusion tube, the lower infusion tube and the air tube in cooperation with the base. In such a manner, the drip rate of the injection is able to be automatically adjusted by the activating module.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An infusion set with capability of controlling quantity of an injection infused to a limb, comprising:
    an infusion device comprising:
        a syringe body comprising a main portion and an auxiliary portion connected to the main portion, an inner chamber being formed in the main portion and configured to contain the injection, the auxiliary portion having a liquid storage space formed therein, the liquid storage space being communicated with the inner chamber, such that the injection contained in the inner chamber is dripped into the liquid storage space;
        an upper infusion tube connecting an upper side of the syringe body with an infusion member, the injection dripping from the infusion member to the inner chamber via the upper infusion tube;
        a lower infusion tube connected to a lower side of the syringe body and configured to be connected to the limb; and
        an air tube connected to the upper side of the syringe body and configured to allow the injection contained in the inner chamber to be infused to the limb via the lower infusion tube; and
    an adjustment device installed on at least one of the upper infusion tube, the lower infusion tube and the air tube, the adjustment device comprising:
        a base disposed on a side of the at least one of the upper infusion tube, the lower infusion tube and the air tube;
        a movable member disposed on another side of the at least one of the upper infusion tube, the lower infusion tube and the air tube, the movable member being movable relative to the base, so as to deform a wall of the at least one of the upper infusion tube, the lower infusion tube and the air tube in cooperation with the base;
    a first detecting module disposed aside the syringe body and configured to detect counts of the injection dripping from the infusion member to the inner chamber, the first detecting module comprising:
        a first light emitting unit disposed on a side of the main portion, the first light emitting unit emitting a light to the main portion in a first light path through a first dripping path along which the injection drips from the infusion member to the inner chamber; and
        a first light receiving unit disposed on another side of the main portion; and
    a second detecting module disposed aside the auxiliary portion and configured to detect counts of the injection dripping from the inner chamber to the liquid storage space, the second detecting module comprising:
        a second light emitting unit disposed on a side of the auxiliary portion, the second light emitting unit emitting a light to the auxiliary portion in a second light path through a second dripping path along which the injection drips from the inner chamber to the liquid storage space; and
        a second light receiving unit disposed on another side of the auxiliary portion.

2. The infusion set of claim 1, wherein the adjustment device is a button set, the base is a mounting member, the movable member is a rotating button rotatable relative to the mounting member, wherein:
    the mounting member has a channel formed therethrough to be mounted with the at least one of the upper infusion tube, the lower infusion tube and the air tube;
    the rotating button comprises:
        a button body mounted with the mounting member in a rotatable manner; and
        a pair of tabs protruding from the button body and rotatable with the button body, the pair of tabs engaging with the at least one of the upper infusion tube, the lower infusion tube and the air tube, so as to twist the wall of the at least one of the upper infusion tube, the lower infusion tube and the air tube in cooperation with the mounting member through rotation of the button body relative to the mounting member.

3. The infusion set of claim 1, wherein the adjustment device is a cam set, the base is a secure member, the movable member is a rotating cam rotatable relative to the secure member, the rotating cam comprises:
    an axis disposed on a side of the at least one of the upper infusion tube, the lower infusion tube and the air tube; and
    a cam body eccentrically mounted with the axis, the cam body pressing the wall of the at least one of the upper infusion tube, the lower infusion tube and the air tube through rotation of the cam body relative to the secure member.

4. The infusion set of claim 1, wherein the adjustment device is a cam set, the base is a secure cam, the movable member is a rotating cam rotatable relative to the secure cam, the rotating cam comprises:
an axis disposed on a side of the at least one of the upper infusion tube, the lower infusion tube and the air tube; and
a cam body eccentrically mounted with the axis, the cam body pressing a wall of the at least one of the upper infusion tube, the lower infusion tube and the air tube through rotation of the cam body relative to the secure cam.

5. The infusion set of claim 1, wherein the adjustment device is a cylinder set, the base is a holding member, the movable member is a cylinder device, the cylinder device comprises:
a cylinder housing disposed on a side of the at least one of the upper infusion tube, the lower infusion tube and the air tube; and
a cylinder head stretchable relative to the cylinder housing, the cylinder head pressing the wall of the at least one of the upper infusion tube, the lower infusion tube and the air tube through the cylinder head stretching out from the cylinder housing.

6. The infusion set of claim 1,
wherein when a drip of the injection on the first dripping path does not interrupt the light in the first light path, the first light receiving unit receives the light emitted from the first light emitting unit and generates a first light strength signal;
wherein when the drip of the injection on the first dripping path interrupts the light in the first light path, the first light receiving unit does not receive the light emitted from the first light emitting unit and generates a second light strength signal;
wherein the first light strength signal, the second light strength signal or a combination thereof is rendered one count of the drip of the injection on the first dripping path.

7. The infusion set of claim 1, wherein the first detecting module further comprises:
a auxiliary light receiving unit disposed aside the first light receiving unit;
wherein when a drip of the injection on the first dripping path does not interrupt the light in the first light path, the first light receiving unit receives the light emitted from the first light emitting unit and generates a first light strength signal;
wherein when the drip of the injection on the first dripping path interrupts the light in the first light path, the first light receiving unit does not receive the light emitted from the first light emitting unit and generates a second light strength signal, and the auxiliary light receiving unit receives the light emitted from the first light emitting unit and refracted by the drip and generates an auxiliary light strength signal;
wherein a coincidence of the second light strength signal and the auxiliary light strength signal is rendered one count of the drip of the injection on the first dripping path.

8. The infusion set of claim 1,
wherein when a drip of the injection on the second dripping path does not interrupt the light in the second light path, the second light receiving unit receives the light emitted from the second light emitting unit and generates a first light strength signal;
wherein when the drip of the injection on the second dripping path interrupts the light in the second light path, the second light receiving unit does not receive the light emitted from the second light emitting unit and generates a second light strength signal;
wherein the first light strength signal, the second light strength signal or a combination thereof is rendered one count of the drip of the injection on the second dripping path.

9. The infusion set of claim 1, wherein the second detecting module further comprises:
a auxiliary light receiving unit disposed aside the second light receiving unit;
wherein when a drip of the injection on the second dripping path does not interrupt the light in the second light path, the second light receiving unit receives the light emitted from the second light emitting unit and generates a first light strength signal;
when the drip of the injection on the second dripping path interrupts the light in the second light path, the second light receiving unit does not receive the light emitted from the second light emitting unit and generates a second light strength signal, and the auxiliary light receiving unit receives the light emitted from the second light emitting unit and refracted by the drip and generates an auxiliary light strength signal;
wherein a coincidence of the second light strength signal and the auxiliary light strength signal is rendered one count of the drip of the injection on the second dripping path.

10. The infusion set of claim 1, wherein further comprising:
an activating unit coupled to the movable member of the adjustment device and configured to drive the movable member to move relative to the base.

11. A system for detecting and controlling drip rate of an infusion device, comprising:
an infusion set of claim 1;
an activating unit coupled to the movable member of the adjustment device installed on the upper infusion tube; and
a control unit coupled to the activating unit and the first detecting module, the control unit rendering counts of the injection dripping from the infusion member to the inner chamber and controlling the activating unit to drive the movable member to move relative to the base based on the counts of the injection dripping from the infusion member to the inner chamber, the control unit further generating information illustrating a relation between the counts of the injection dripping from the infusion member to the inner chamber and an rotating angle of the movement member.

12. The system of claim 11, wherein:
when a drip of the injection on the first dripping path does not interrupt the light in the first light path, the first light receiving unit receives the light emitted from the first light emitting unit and generates a first light strength signal;
when the drip of the injection on the first dripping path interrupts the light in the first light path, the first light receiving unit does not receive the light emitted from the first light emitting unit and generates a second light strength signal;
the first light strength signal, the second light strength signal or a combination thereof is rendered one count of the drip of the injection on the first dripping path.

13. The system of claim 11, wherein the first detecting module further comprises:
a auxiliary light receiving unit disposed aside the first light receiving unit;

when the drip of the injection on the first dripping path interrupts the light in the first light path, the first light receiving unit does not receive the light emitted from the first light emitting unit and generates a light strength signal, and the auxiliary light receiving unit receives the light emitted from the first light emitting unit and refracted by the drip and generates an auxiliary light strength signal;

wherein a coincidence of the light strength signal and the auxiliary light strength signal is rendered one count of the drip of the injection on the first dripping path.

14. A system for detecting and controlling drip rate of an infusion device, comprising:

an infusion set of claim 1;

an activating unit coupled to the movable member of the adjustment device installed on the lower infusion tube; and a control unit coupled to the activating unit and the second detecting module, the control unit rendering counts of the injection dripping from the inner chamber to the liquid storage space and controlling the activating unit to drive the movable member to move relative to the base based on the counts of the injection dripping from the inner chamber to the liquid storage space, the control unit further generating information illustrating a relation between the counts of the injection dripping from the inner chamber to the liquid storage space and an rotating angle of the movement member.

15. The system of claim 14, wherein:

when a drip of the injection on the second dripping path does not interrupt the light in the second light path, the second light receiving unit receives the light emitted from the second light emitting unit and generates a first light strength signal;

when the drip of the injection on the second dripping path interrupts the light in the second light path, the second light receiving unit does not receive the light emitted from the second light emitting unit and generates a second light strength signal;

the first light strength signal, the second light strength signal or a combination thereof is rendered one count of the drip of the injection on the second dripping path.

16. The system of claim 14, wherein the second detecting module further comprises:

a auxiliary light receiving unit disposed aside the second light receiving unit;

when the drip of the injection on the second dripping path interrupts the light in the second light path, the second light receiving unit does not receive the light emitted from the second light emitting unit and generates a light strength signal, and the auxiliary light receiving unit receives the light emitted from the second light emitting unit and refracted by the drip and generates an auxiliary light strength signal;

wherein a coincidence of the light strength signal and the auxiliary light strength signal is rendered one count of the drip of the injection on the second dripping path.

* * * * *